(12) United States Patent
Beetz et al.

(10) Patent No.: US 10,850,244 B2
(45) Date of Patent: *Dec. 1, 2020

(54) LOW TEMPERATURE SPRAY DRYING OF CARRIER-FREE COMPOSITIONS

(71) Applicant: ZoomEssence, Inc., Hebron, KY (US)

(72) Inventors: Charles Pershing Beetz, Butler, KY (US); Jason Andrew Beetz, California, KY (US); Daniel Michael Schlipf, Edgewood, KY (US); Jason Zhixin Li, Union, KY (US)

(73) Assignee: ZOOMESSENCE, INC., Hebron, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/800,961

(22) Filed: Feb. 25, 2020

(65) Prior Publication Data

US 2020/0206707 A1    Jul. 2, 2020

Related U.S. Application Data

(63) Continuation of application No. 15/965,910, filed on Apr. 28, 2018, now Pat. No. 10,569,244.

(51) Int. Cl.
 *A23C 1/04*    (2006.01)
 *A23L 2/10*    (2006.01)
 (Continued)

(52) U.S. Cl.
 CPC ............... *B01J 2/06* (2013.01); *A61K 9/1688* (2013.01); *B01D 1/18* (2013.01); *A23C 1/04* (2013.01);
 (Continued)

(58) Field of Classification Search
 CPC .... B01D 1/16; B01D 1/18; B01D 1/20; A23C 1/04; A23C 1/045; A23C 1/05;
 (Continued)

(56) References Cited

U.S. PATENT DOCUMENTS 1,829,477 A   10/1925  Douthitt
2,287,995 A    6/1942  Haugh
(Continued)

FOREIGN PATENT DOCUMENTS

AU       549614 B2    2/1986
CA      1162699 A     2/1984
(Continued)

OTHER PUBLICATIONS

GEA Processing Engineering, Inc., "GEA Powder Technology Division: Niro: Spray Drying", "Accessed via http://www.niroinc.com/html/drying/fdpdfs/480gbspraydrying.pdf", Aug. 22, 2002, pp. 1-15.
(Continued)

*Primary Examiner* — Jonathan Luke Pilcher
(74) *Attorney, Agent, or Firm* — Hultquist, PLLC; Steven J. Hultquist

(57) ABSTRACT

A spray drying process and apparatus for drying a spray dryable liquid composition to a spray dried powder is described, in which the spray dryable liquid composition contains no carrier. The spray dryable liquid composition is processed at a solids concentration not exceeding 80% by weight, based on total weight of the spray dryable liquid composition, being atomized to generate an atomized spray of liquid particles of the spray dryable liquid composition into a spray drying chamber, in which the atomized spray is contacted with a stream of drying fluid flowed at temperature not exceeding 100° C. into the spray drying chamber, to form the spray dried powder.

20 Claims, 1 Drawing Sheet

(51) Int. Cl.
*B01D 1/18* (2006.01)
*B01J 2/06* (2006.01)
*A61K 9/16* (2006.01)
*B01D 1/16* (2006.01)
*A23L 2/08* (2006.01)

(52) U.S. Cl.
CPC . *A23L 2/08* (2013.01); *A23L 2/10* (2013.01); *A23L 2/102* (2013.01); *B01D 1/16* (2013.01)

(58) Field of Classification Search
CPC ..... A23C 1/12; A23L 2/08; A23L 2/10; A23L 2/102; B05B 16/00; B05B 16/20
USPC ..... 159/3, 4.01, 4.02, 4.03, 4.04, 4.05, 4.06, 159/4.07, 4.08, 4.09, 4.1, 4.2, 4.3, 4.4
See application file for complete search history.

(56) References Cited

U.S. PATENT DOCUMENTS

| | | |
|---|---|---|
| 2,326,142 A | 8/1943 | Hall |
| 2,884,049 A | 4/1959 | Barzelay |
| 2,911,036 A | 11/1959 | Lazar et al. |
| 2,954,293 A | 9/1960 | Rusoff |
| 3,554,768 A | 1/1971 | Feldman |
| 3,615,723 A | 10/1971 | Meade et al. |
| 3,620,776 A | 11/1971 | Mishkin et al. |
| 3,655,397 A | 4/1972 | Parliment et al. |
| 3,677,321 A | 7/1972 | Felstead |
| 3,679,416 A | 7/1972 | Reich |
| 3,740,865 A | 6/1973 | Laguilharre |
| 3,741,273 A | 6/1973 | Meade |
| 3,805,869 A | 4/1974 | Winter et al. |
| 3,817,308 A | 6/1974 | Bundo |
| 3,840,996 A | 10/1974 | Grindstaff et al. |
| 3,844,969 A | 10/1974 | Griffiths et al. |
| 3,886,297 A | 5/1975 | Parliment et al. |
| 3,920,815 A | 11/1975 | Harvey et al. |
| 3,956,521 A | 5/1976 | Pisecky et al. |
| 3,962,321 A | 6/1976 | Parliment et al. |
| 3,962,384 A | 6/1976 | Cannalonga et al. |
| 3,963,559 A | 6/1976 | Petersen et al. |
| 3,966,975 A | 6/1976 | Hansen et al. |
| 4,001,437 A | 1/1977 | Jaeggi et al. |
| 4,032,465 A | 6/1977 | Bauer et al. |
| 4,062,641 A | 12/1977 | Hovmand et al. |
| 4,070,766 A | 1/1978 | Kamphuis |
| 4,072,570 A | 2/1978 | Williams |
| 4,099,982 A | 7/1978 | Hansen et al. |
| 4,141,783 A | 2/1979 | Pisecky et al. |
| 4,198,308 A | 4/1980 | Micciche |
| 4,226,670 A | 10/1980 | Ferguson et al. |
| 4,261,793 A | 4/1981 | Nakamura et al. |
| 4,276,312 A | 6/1981 | Merritt |
| 4,281,024 A | 7/1981 | Hauberg et al. |
| 4,302,481 A | 11/1981 | Ribnitz et al. |
| 4,362,273 A | 12/1982 | Seino et al. |
| 4,420,442 A | 12/1983 | Sands |
| 4,422,900 A | 12/1983 | Bordelon et al. |
| 4,438,147 A | 3/1984 | Hedrick, Jr. |
| 4,454,165 A | 6/1984 | Sato et al. |
| 4,476,042 A | 10/1984 | Sprecker et al. |
| 4,476,147 A | 10/1984 | Hall et al. |
| 4,481,221 A | 11/1984 | Mookherjee et al. |
| 4,481,224 A | 11/1984 | Muralidhara et al. |
| 4,490,403 A | 12/1984 | Pisecky et al. |
| 4,493,750 A | 1/1985 | Olmsted et al. |
| 4,511,592 A | 4/1985 | Percel et al. |
| 4,515,987 A | 5/1985 | Boden et al. |
| 4,520,032 A | 5/1985 | Hall et al. |
| 4,521,613 A | 6/1985 | Pittet et al. |
| 4,521,634 A | 6/1985 | Fujioka et al. |
| 4,522,765 A | 6/1985 | Wiegers et al. |
| 4,524,010 A | 6/1985 | Reuter et al. |
| 4,525,364 A | 6/1985 | Wiegers et al. |
| 4,532,145 A | 7/1985 | Saleeb et al. |
| 4,532,364 A | 7/1985 | Fujioka et al. |
| 4,535,192 A | 8/1985 | Hall et al. |
| 4,537,704 A | 8/1985 | Sprecker et al. |
| 4,539,143 A | 9/1985 | Boden et al. |
| 4,539,209 A | 9/1985 | Wilson et al. |
| 4,544,775 A | 10/1985 | Fujioka et al. |
| 4,548,821 A | 10/1985 | Hall et al. |
| 4,552,770 A | 11/1985 | Pittet et al. |
| 4,565,707 A | 1/1986 | Pittet et al. |
| 4,568,538 A | 2/1986 | Boden et al. |
| 4,571,344 A | 2/1986 | Pittet et al. |
| 4,600,576 A | 7/1986 | Pittet et al. |
| 4,613,511 A | 9/1986 | Pittet et al. |
| 4,614,831 A | 9/1986 | Sprecker et al. |
| 4,619,780 A | 10/1986 | Fujioka et al. |
| 4,620,945 A | 11/1986 | Mookherjee et al. |
| 4,623,538 A | 11/1986 | Pittet et al. |
| 4,623,547 A | 11/1986 | Pittet et al. |
| 4,626,440 A | 12/1986 | Pittet et al. |
| 4,629,586 A | 12/1986 | Wilson et al. |
| 4,629,805 A | 12/1986 | Sprecker et al. |
| 4,632,831 A | 12/1986 | Hall |
| 4,643,903 A | 2/1987 | Sprecker et al. |
| 4,661,281 A | 4/1987 | Seiter et al. |
| 4,677,207 A | 6/1987 | Boden et al. |
| 4,679,733 A | 7/1987 | Lipp |
| 4,680,142 A | 7/1987 | Pittet et al. |
| 4,681,976 A | 7/1987 | Sprecker et al. |
| 4,702,799 A | 10/1987 | Tuot |
| 4,724,121 A | 2/1988 | Weyand |
| 4,762,636 A | 8/1988 | Balliello et al. |
| 4,794,193 A | 12/1988 | Pittet et al. |
| 4,804,496 A | 2/1989 | Lowery et al. |
| 4,840,801 A | 6/1989 | Mookherjee et al. |
| 4,849,125 A | 7/1989 | Seiter et al. |
| 4,865,853 A | 9/1989 | Mookherjee et al. |
| 4,873,112 A | 10/1989 | Mitchell et al. |
| 4,883,884 A | 11/1989 | Boden et al. |
| 4,892,910 A | 1/1990 | Klesse et al. |
| 4,931,203 A | 6/1990 | Ahmed et al. |
| 4,936,901 A | 6/1990 | Surgant et al. |
| 4,950,495 A | 8/1990 | Boden et al. |
| 4,962,089 A | 10/1990 | Boden et al. |
| 4,983,579 A | 1/1991 | Boden et al. |
| 5,004,618 A | 4/1991 | Buckholz, Jr. et al. |
| 5,067,655 A | 11/1991 | Farago et al. |
| 5,094,860 A | 3/1992 | Newhall et al. |
| 5,100,509 A | 3/1992 | Pisecky et al. |
| 5,124,162 A | 6/1992 | Boskovic et al. |
| 5,130,149 A | 7/1992 | Keller et al. |
| 5,137,741 A | 8/1992 | Zampino et al. |
| 5,153,011 A | 10/1992 | Patel et al. |
| 5,196,219 A | 3/1993 | Hsu et al. |
| 5,227,017 A | 7/1993 | Tanaka et al. |
| 5,338,553 A | 8/1994 | Johnson et al. |
| 5,354,742 A | 10/1994 | Deming et al. |
| 5,391,647 A | 2/1995 | Yamamoto et al. |
| 5,443,829 A | 8/1995 | Kensil et al. |
| 5,445,839 A | 8/1995 | Hagiwara et al. |
| 5,462,978 A | 10/1995 | Penzel et al. |
| 5,506,353 A | 4/1996 | Subramaniam |
| 5,525,367 A | 6/1996 | King et al. |
| 5,593,715 A | 1/1997 | Christensen |
| 5,596,817 A | 1/1997 | Hansen et al. |
| 5,702,749 A | 12/1997 | Sugiura et al. |
| 5,723,424 A | 3/1998 | Jennings |
| 5,759,599 A | 6/1998 | Wampler et al. |
| 5,773,061 A | 6/1998 | Getler et al. |
| 5,786,017 A | 7/1998 | Blake et al. |
| 5,840,360 A | 11/1998 | Larsen |
| 5,891,473 A | 4/1999 | Stanier |
| 5,968,575 A | 10/1999 | Rasmussen |
| 6,048,565 A | 4/2000 | Getler et al. |
| 6,058,624 A | 5/2000 | Bach et al. |
| 6,077,543 A | 6/2000 | Gordon et al. |
| 6,200,949 B1 | 3/2001 | Reijmer et al. |
| 6,237,247 B1 | 5/2001 | Van Den Meersche |
| 6,251,463 B1 | 6/2001 | Rossy et al. |

(56) References Cited

U.S. PATENT DOCUMENTS

| | | |
|---|---|---|
| 6,253,463 B1 | 7/2001 | Hansen |
| 6,325,859 B1 | 12/2001 | De Roos et al. |
| 6,335,045 B1 | 1/2002 | Peters et al. |
| 6,387,431 B1 | 5/2002 | Gautschi |
| 6,391,361 B1 | 5/2002 | Peters et al. |
| RE37,860 E | 9/2002 | Blake et al. |
| 6,474,573 B1 | 11/2002 | Kelly |
| 6,482,433 B1 | 11/2002 | DeRoos et al. |
| 6,497,911 B1 | 12/2002 | Hansen et al. |
| 6,560,897 B2 | 5/2003 | Chickering et al. |
| 6,582,728 B1 | 6/2003 | Platz et al. |
| 6,607,771 B2 | 8/2003 | Benczedi et al. |
| 6,607,778 B2 | 8/2003 | Mutka et al. |
| 6,608,017 B1 | 8/2003 | Dihora et al. |
| 6,649,267 B2 | 11/2003 | Agawa et al. |
| 6,652,898 B2 | 11/2003 | Jensen |
| 6,656,394 B2 | 12/2003 | Kelly |
| 6,689,755 B1 | 2/2004 | Gabel et al. |
| 6,723,359 B2 | 4/2004 | Subramaniam et al. |
| 6,734,158 B2 | 5/2004 | Starkenmann |
| 6,763,607 B2 | 7/2004 | Beyerinck R et al. |
| 6,769,200 B2 | 8/2004 | Raehse et al. |
| 6,838,100 B2 | 1/2005 | Jaeger et al. |
| 6,902,751 B1 | 6/2005 | Schleifenbaum et al. |
| 6,929,814 B2 | 8/2005 | Bouwmeesters et al. |
| 6,933,265 B2 | 8/2005 | Marty |
| 6,962,006 B2 | 11/2005 | Chickering, III et al. |
| 6,964,385 B2 | 11/2005 | Kelly |
| 7,022,665 B2 | 4/2006 | Decorzant et al. |
| 7,090,832 B2 | 8/2006 | Zanone et al. |
| 7,097,872 B2 | 8/2006 | Dewis et al. |
| 7,128,936 B1 | 10/2006 | Hansen |
| 7,176,176 B2 | 2/2007 | Pickenhagen et al. |
| 7,176,177 B2 | 2/2007 | Lambrecht et al. |
| 7,204,998 B2 | 4/2007 | Holzner et al. |
| 7,252,848 B2 | 8/2007 | Gelin |
| 7,316,826 B2 | 1/2008 | Kindel et al. |
| 7,332,468 B2 | 2/2008 | Widder et al. |
| 7,348,035 B2 | 3/2008 | Schleifenbaum et al. |
| 7,361,376 B2 | 4/2008 | Dewis et al. |
| 7,378,121 B2 | 5/2008 | Ley et al. |
| 7,473,433 B2 | 1/2009 | Weikert et al. |
| 7,534,460 B2 | 5/2009 | Dewis et al. |
| 7,651,713 B2 | 1/2010 | Keller |
| 8,003,147 B1 | 8/2011 | Nelson et al. |
| 8,753,643 B1 | 6/2014 | Poe et al. |
| 8,939,388 B1 | 1/2015 | Beetz et al. |
| 9,308,245 B2 | 4/2016 | Poe et al. |
| 9,332,776 B1 | 5/2016 | Beetz et al. |
| 9,551,527 B2 | 1/2017 | Beetz et al. |
| 9,861,945 B1 | 1/2018 | Beetz et al. |
| 9,993,787 B1 | 6/2018 | Beetz et al. |
| 10,155,234 B1 | 12/2018 | Beetz et al. |
| 10,252,181 B2 | 4/2019 | Beetz et al. |
| 10,486,173 B2 | 11/2019 | Beetz et al. |
| 10,569,244 B2 | 2/2020 | Beetz et al. |
| 10,625,281 B2 * | 4/2020 | Beetz ............... B05B 5/032 |
| 2002/0187221 A1 | 12/2002 | Tanaka et al. |
| 2003/0003212 A1 | 1/2003 | Tsuji et al. |
| 2003/0021883 A1 | 1/2003 | Skiff |
| 2003/0075012 A1 | 4/2003 | Knunz et al. |
| 2003/0082272 A1 | 5/2003 | Bouwmeesters et al. |
| 2003/0192815 A1 | 10/2003 | Kelly |
| 2003/0196957 A1 | 10/2003 | Henningfield et al. |
| 2003/0205629 A1 | 11/2003 | Kelly |
| 2004/0062845 A1 | 4/2004 | Krawczyk et al. |
| 2004/0253343 A1 | 12/2004 | Ha et al. |
| 2005/0031769 A1 | 2/2005 | Watanabe et al. |
| 2005/0051917 A1 | 3/2005 | Grothe et al. |
| 2005/0209443 A1 | 9/2005 | Bolen et al. |
| 2005/0282728 A1 | 12/2005 | Narula et al. |
| 2006/0035008 A1 | 2/2006 | Virgallito et al. |
| 2006/0040023 A1 | 2/2006 | Zeller et al. |
| 2006/0159818 A1 | 7/2006 | Kunieda |
| 2006/0264130 A1 | 11/2006 | Karles et al. |
| 2007/0054837 A1 | 3/2007 | Weiss et al. |
| 2007/0078071 A1 | 4/2007 | Lee et al. |
| 2007/0117727 A1 | 5/2007 | Narula et al. |
| 2007/0166185 A1 | 7/2007 | Bartels |
| 2007/0184163 A1 | 8/2007 | Toth et al. |
| 2007/0218012 A1 | 9/2007 | Bittorf et al. |
| 2007/0218179 A1 | 9/2007 | Ott et al. |
| 2007/0231424 A1 | 10/2007 | Castro et al. |
| 2007/0297993 A1 | 12/2007 | Kindel et al. |
| 2008/0008801 A1 | 1/2008 | Barnekow et al. |
| 2008/0015264 A1 | 1/2008 | Schleifenbaum et al. |
| 2008/0057175 A1 | 3/2008 | Barnekow et al. |
| 2008/0063747 A1 | 3/2008 | Boghani et al. |
| 2008/0064625 A1 | 3/2008 | Holscher |
| 2008/0081779 A1 | 4/2008 | Holscher |
| 2008/0107786 A1 | 5/2008 | Barnekow et al. |
| 2008/0113073 A1 | 5/2008 | Ley et al. |
| 2008/0199592 A1 | 8/2008 | Fexer et al. |
| 2008/0214675 A1 | 9/2008 | Ley et al. |
| 2008/0220140 A1 | 9/2008 | Ley et al. |
| 2008/0227866 A1 | 9/2008 | Ley et al. |
| 2008/0241322 A1 | 10/2008 | Bunge |
| 2008/0242585 A1 | 10/2008 | Ott et al. |
| 2008/0242740 A1 | 10/2008 | Ley et al. |
| 2008/0292763 A1 | 11/2008 | Looft et al. |
| 2008/0305052 A1 | 12/2008 | Ley et al. |
| 2008/0317923 A1 | 12/2008 | Ley et al. |
| 2009/0048206 A1 | 2/2009 | Watanabe et al. |
| 2009/0081140 A1 | 3/2009 | Brocke et al. |
| 2009/0091049 A1 | 4/2009 | Nielsen |
| 2009/0092725 A1 | 4/2009 | Panten et al. |
| 2009/0110796 A1 | 4/2009 | Backes et al. |
| 2009/0124701 A1 | 5/2009 | Langer et al. |
| 2009/0155445 A1 | 6/2009 | Le et al. |
| 2009/0155446 A1 | 6/2009 | Reiss et al. |
| 2009/0163403 A1 | 6/2009 | Levorse, Jr. et al. |
| 2009/0163404 A1 | 6/2009 | Levorse, Jr. et al. |
| 2009/0252789 A1 | 10/2009 | Trophardy |
| 2009/0291176 A1 | 11/2009 | Nagao et al. |
| 2010/0055267 A1 | 3/2010 | Popplewell et al. |
| 2010/0196493 A1 | 8/2010 | Buisson |
| 2010/0230840 A1 | 9/2010 | Murkunde et al. |
| 2011/0059205 A1 | 3/2011 | Gaysinsky et al. |
| 2011/0064783 A1 | 3/2011 | Bang-Madsen et al. |
| 2012/0027915 A1 | 2/2012 | Van Eert et al. |
| 2013/0022728 A1 | 1/2013 | Popplewell et al. |
| 2014/0014276 A1 | 1/2014 | Sorensen et al. |
| 2014/0193562 A1 | 7/2014 | Popplewell et al. |
| 2014/0205713 A1 | 7/2014 | Hans et al. |
| 2014/0242116 A1 | 8/2014 | Poe et al. |
| 2014/0284001 A1 | 9/2014 | Amstad et al. |
| 2016/0051956 A1 | 2/2016 | Penth et al. |
| 2016/0223255 A1 | 8/2016 | Beetz et al. |
| 2016/0271513 A1 | 9/2016 | Weitz et al. |
| 2017/0120267 A1 | 5/2017 | Ackerman et al. |
| 2017/0312726 A1 | 11/2017 | Sobel et al. |
| 2019/0329201 A1 | 10/2019 | Beetz et al. |

FOREIGN PATENT DOCUMENTS

| | | |
|---|---|---|
| CA | 1334460 C | 3/1989 |
| CA | 1314432 C | 3/1993 |
| CA | 2171389 C | 3/1996 |
| CA | 2258751 C | 12/1997 |
| CA | 2253154 C | 5/1999 |
| CA | 2321660 C | 9/1999 |
| CA | 2407614 C | 11/2001 |
| CA | 2663386 A1 | 4/2008 |
| EP | 0322137 A1 | 6/1989 |
| EP | 0344375 B1 | 12/1989 |
| EP | 0232313 B1 | 5/1990 |
| EP | 0180366 B1 | 6/1990 |
| EP | 0420509 A1 | 4/1991 |
| EP | 0227486 B1 | 11/1991 |
| EP | 0515478 B1 | 12/1993 |
| EP | 0429482 B1 | 4/1994 |
| EP | 0461197 B1 | 6/1994 |
| EP | 0517423 B1 | 3/1995 |
| EP | 0366898 B1 | 2/1996 |

(56) References Cited

FOREIGN PATENT DOCUMENTS

| | | |
|---|---|---|
| EP | 0619075 B1 | 1/1997 |
| EP | 0832695 A2 | 4/1998 |
| EP | 1064856 A2 | 1/2001 |
| EP | 1106081 A1 | 6/2001 |
| EP | 1280591 B1 | 12/2006 |
| EP | 1435797 B1 | 8/2007 |
| EP | 2052622 A1 | 4/2009 |
| EP | 2138567 A1 | 12/2009 |
| EP | 3059537 A1 | 8/2016 |
| FR | 2675666 A1 | 10/1992 |
| GB | 575118 A | 2/1946 |
| GB | 1015599 A | 1/1966 |
| GB | 2364714 A | 2/2002 |
| IE | 62024 B1 | 12/1994 |
| WO | 9117821 A1 | 11/1991 |
| WO | 9428181 A2 | 12/1994 |
| WO | 9513864 A1 | 5/1995 |
| WO | 9517174 A1 | 6/1995 |
| WO | 9713416 A1 | 4/1997 |
| WO | 9714288 A2 | 4/1997 |
| WO | 9733485 A1 | 9/1997 |
| WO | 9804243 A1 | 2/1998 |
| WO | 0167897 A1 | 9/2001 |
| WO | 0207541 A1 | 1/2002 |
| WO | 2005063032 A1 | 7/2005 |
| WO | 2006082536 A1 | 8/2006 |
| WO | 2007054853 A1 | 5/2007 |
| WO | 2007096790 A1 | 8/2007 |
| WO | 2007135583 A2 | 11/2007 |
| WO | 2008047301 A1 | 4/2008 |
| WO | 2008077399 A1 | 7/2008 |
| WO | 2008113778 A1 | 9/2008 |
| WO | 2010104713 A1 | 9/2010 |
| WO | 2011121468 A1 | 10/2011 |
| WO | 2012122010 A2 | 9/2012 |
| WO | 2016064608 A1 | 4/2016 |
| WO | 2016123224 A1 | 8/2016 |
| WO | WO2017167966 A1 | 10/2017 |
| WO | WO2018066835 A1 | 4/2018 |

OTHER PUBLICATIONS

Gohel, M., et al., "Spray Drying: A Review", "Pharmaceutical Reviews", Sep. 28, 2009, pp. 1-20, vol. 7, No. 5.

Gomez, A., et al., "Charge and fission of droplets in electrostatic sprays", "Phys. Fluids", Jan. 1994, pp. 404-414, vol. 6, No. 1.

Goula, A., et al., "Spray Drying of Tomato Pulp: Effect of Feed Concentration", "Drying Technology", 2004, pp. 2309-2330, vol. 22, No. 10.

"Merriam-Webster Dictionary Definition of 'Hygroscopic'", "http://www.merriam-webster.com/dictionary/hygroscopic (Accessed: Nov. 17, 2015)".

Jongsma, F., et al., "Large Eddy Simulation of Unsteady Turbulent Flow in a Semi-Industrial Size Spray Dryer", "Dairy Sci. and Technol.", 2013, pp. 373-386, vol. 93.

Killeen, M., "The Process of Spray Drying and Spray Congealing", "Pharmaceutical Engineering", Jul./Aug. 1993, pp. 56 58-62, 64, vol. 13.

Lacagnina, G., et al., "Experimental Study on the Forcing Design for an Intermittent Injection", "Experiments in Fluids", 2018, pp. 1-15, vol. 59, No. 123.

Langrish, T., et al., "Spray drying of food ingredients and applications of CFD in spray drying", "Chemical Engineering and Processing", 2001, pp. 345-354, vol. 40.

Leuenberger, H., "Spray freeze-drying—the process of choice for low water soluble drugs?", "Journal of Nanoparticle Research", 2002, pp. 111-119, vol. 4.

Moeller, J., et al., "A Primer on Spray Drying", "Chemical Engineering", Nov. 2009, pp. 34-40.

Mumenthaler, M., et al., "Atmospheric spray-freeze drying: a suitable alternative in freeze-drying technology", "International Journal of Pharmaceutics", 1991, pp. 97-110, vol. 72.

Rayleigh, L., "XX. On the Equilibrium of Liquid Conducting Masses Charged With Electricity", "Philosophical Magazine Series 5", 1882, pp. 184-186, vol. 14, No. 87.

Sirignano, W., "Fluid Dynamics and Transport of Droplets and Sprays, Second Edition", Jan. 2010, p. 34, Publisher: Cambridge University Press.

Westergaard, V., "The New Niro Integrated Filter Dryer IFD", "Danish Dairy and Food Industry . . . worldwide", Sep. 2002, pp. 62-64.

Zbicinski, I., et al., "Effect of Turbulence on Heat and Mass Transfer in the Atomization Zone", "Drying Technology", 1996, pp. 231-244, vol. 14, No. 2, Publisher: Taylor & Grancis Group.

Beetz, C., et al., "Ultrahigh Efficiency Spray Drying Apparatus and Process", Jun. 11, 2018.

Beetz, C., et al., "Ultrahigh Efficiency Spray Drying Apparatus and Process", Aug. 4, 2018.

Bailey, A., "Electrostatic Spraying of Liquids", Apr. 1988, pp. 1-35, Publisher: Research Studies Press Ltd., Published in: Taunton, Somerset, England.

Baranauskiene, R., et al., "Flavor Retention of Peppermint (*Mentha piperita* L.) Essential Oil Spray-Dried in Modified Starches during Encapsulation and Storage", "Journal of Agricultural and Food Chemistry", Mar. 24, 2007, pp. 3027-3036, vol. 55.

Beetz, C., et al., "U.S. Appl. No. 16/005,302, Ultrahigh Efficiency Spay Drying Apparatus and Process, filed Jun. 11, 2018".

Broadhead, J., et al., "The Spray Drying of Pharmaceuticals", "Drug Development and Industrial Pharmacy", 1992, pp. 1169-1206, vol. 18, No. 11 and 12.

Coumans, W., et al., "Theoretical and Practical Aspects of Aroma Retention in Spray Drying and Freeze Drying", "Drying Technology", 1994, pp. 99-149, vol. 12, No. 1 and 2.

"Decision Granting Institution of Inter Partes Review filed on Dec. 15, 2015 for U.S. Pat. No. 8,939,388 (IPR2015-01418)".

Dobry, D., et al., "A Model-Based Methodology for Spray-Drying Process Development", "J. Pharm. Innov.", Jul. 25, 2009, pp. 133-142, vol. 4.

\* cited by examiner

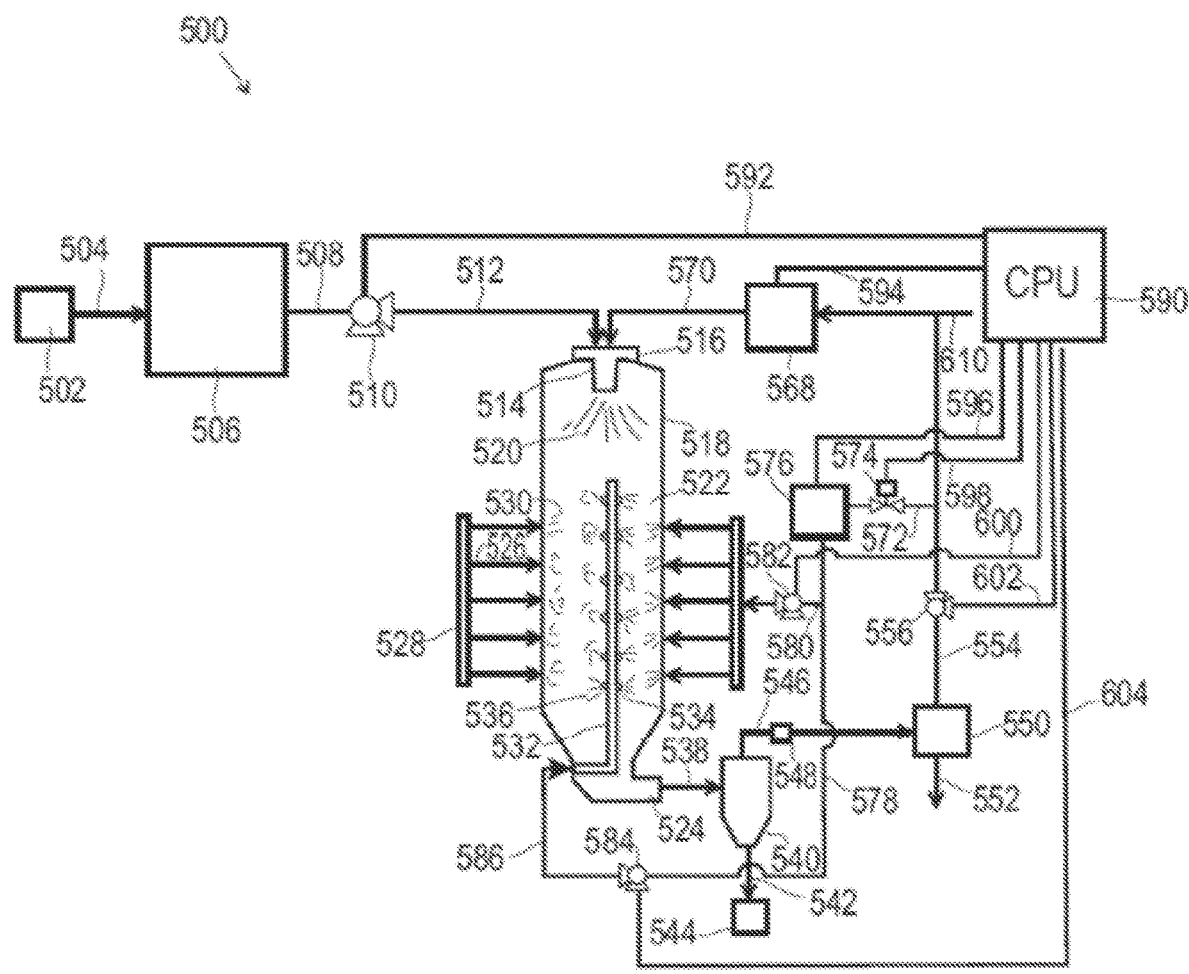

LOW TEMPERATURE SPRAY DRYING OF CARRIER-FREE COMPOSITIONS

CROSS-REFERENCE TO RELATED APPLICATION

This is a continuation under 35 USC § 120 of U.S. patent application Ser. No. 15/965,910 filed Apr. 28, 2018 in the names of Charles Pershing Beetz, Jason Andrew Beetz, Daniel Michael Schlipf, and Jason Zhixin Li for LOW TEMPERATURE SPRAY DRYING OF CARRIER-FREE COMPOSITIONS. The disclosure of U.S. patent application Ser. No. 15/965,910 is hereby incorporated herein by reference, in its entirety, for all purposes.

BACKGROUND

Field of the Disclosure

The disclosure relates to low temperature spray drying in carrier-free compositions are spray dried to a spray dried powder, and has particular utility to the processing of thermally sensitive materials.

Description of the Related Art

Spray drying has existed as a basic materials processing operation since the late 1800s, and has been continually refined since that time. The spray drying operation may be of varied character, but typically involves injecting a liquid composition of material into a chamber for contact with a drying fluid concurrently flowed through the chamber. The injected wet material in the form of droplets contacts the stream of drying fluid so that the liquid passes from the droplets to the drying fluid stream, producing a spray dried product that is discharged from the drying chamber, and drying fluid effluent that likewise is discharged from the drying chamber.

In prior spray drying operations, it has been conventional practice to provide the drying fluid as a gas at high elevated temperature, e.g., temperatures on the order of 180-200° C., in order to produce dry powder products. The drying fluid has conventionally been air, and the material to be spray dried may be provided in a dryable liquid form, e.g., as a neat liquid material, or the material may be a solid in a spray drying liquid composition of slurry, suspension, emulsion, or solution form, which may additionally include carrier material with which the spray dried product is associated at the conclusion of the spray drying process. In various applications, the material to be spray dried is present in a slurry containing solvent, e.g., water, alcohol, or other appropriate liquid, as well as a carrier material, such as carbohydrate, cellulosic, wax, gum, protein, or other suitable material. To effect the spray drying operation, the spray drying composition is injected into the drying chamber using a nozzle, atomizer, or the like, to form a spray of fine droplets for contacting with the drying fluid that is flowed into and through the drying chamber.

The aforementioned high elevated temperature levels on the order of 180-200° C. for the drying fluid have been conventional practice in the art, in order to rapidly heat the droplets of spray dried material and volatilize the liquid therefrom for production of spray dried powder. Such high temperature levels, however, limit the applicability of the spray drying operation to spray dryable materials that are thermally stable or otherwise are not severely adversely affected at the high temperatures of the spray drying operation. A wide variety of materials can accommodate the high temperature regime of the spray drying operation, but suffer losses of material (through volatilization of the product material at high temperature) and/or otherwise are degraded in physical properties and/or performance characteristics as a result of their high temperature exposure during the spray drying operation. In such respect, the conventional spray drying practice has recognized limitations and deficiencies.

Against the foregoing context, the low temperature spray drying apparatus and process disclosed in ZoomEssence, Inc.'s U.S. Pat. Nos. 8,939,388, 9,332,776, and 9,551,527 embody a substantial advance in the art involving starch carriers. As disclosed in such patents, spray drying is carried out at spray drying conditions including inlet temperature of the drying fluid below 100° C., and even down to ambient temperature in some applications, utilizing spray drying slurries including starch carrier, active ingredient, and solvent, in which the slurry has viscosity above about 300 mPa-sec, slurry water content not exceeding 50% by weight of the slurry, and low humidity of the drying fluid introduced to the drying system. Such starch-based slurry spray drying operation, conducted at low temperature spray drying conditions markedly different from the conventional practice of the art, enables spray drying to be utilized for a myriad of products that would otherwise be contraindicated by the elevated temperature conditions of conventional high temperature spray drying practice.

There exist, however, a large population of materials that is not amenable to starch-based slurry spray drying.

SUMMARY

The present disclosure relates to spray drying of carrier-free compositions at low temperature.

As discussed in the Background section hereof, U.S. Pat. Nos. 8,939,388, 9,332,776, and 9,551,527 embody a substantial advance in the art involving spray drying of slurries containing starch carrier, active ingredient, and solvent, to produce spray dried active ingredients encapsulated by the starch carrier. Starch carrier slurries processed by spray drying involve substantial amounts of starch in the spray dryable feedstock A priori, it is not evident that a corresponding low temperature process could be effectively utilized to achieve spray dried powder products of the superior character that have been found to be achievable where no carrier is present, without hydrodynamic enhancement in the spray drying chamber or the provision of excessively long residence times in the spray drying chamber, since active ingredients are not supported by the presence of carriers in the formation of particles and therefore must be dried to even higher standards of solvent minimization.

It has been surprisingly and unexpectedly found, however, that low temperature spray drying can be effectuated in a remarkably effective manner, when the spray drying process is carried out with a carrier-free feedstock of the active ingredient and solvent, in which the drying fluid, which may for example be air, nitrogen, oxygen, helium, argon, carbon dioxide, or other suitable gas or gas mixture, is introduced to a spray drying chamber at a drying fluid temperature T (° C.) not exceeding 100° C., to achieve spray dried powder products of the aforementioned superior character.

In one aspect, the present disclosure relates to a spray drying process for drying a spray dryable liquid composition to a spray dried powder, wherein the spray dryable liquid composition contains no carrier, the process comprising:

providing the spray dryable liquid composition at a solids concentration not exceeding 80% by weight, based on total weight of the spray dryable liquid composition;

atomizing the spray dryable liquid composition to generate an atomized spray of liquid particles of the spray dryable liquid composition into a spray drying chamber;

flowing a stream of drying fluid at temperature not exceeding 100° C. into the spray drying chamber for flow through the spray drying chamber, to contact the spray of liquid particles therein for drying of the liquid particles to form the spray dried powder; and discharging from the spray drying chamber effluent drying fluid and the spray dried powder dried by contact with the drying fluid in the spray drying chamber.

In another aspect, the disclosure relates to a spray drying system constructed and arranged to carry out the above-described carrier-free spray drying process.

Other aspects, features and embodiments of the disclosure will be more fully apparent from the ensuing description and appended claims.

BRIEF DESCRIPTION OF THE DRAWINGS

FIG. 1 is a schematic representation of a spray drying process system according to one embodiment of the present disclosure.

DETAILED DESCRIPTION

The present disclosure relates to low temperature (<100° C.) spray drying of carrier-free spray dryable liquid compositions to form a spray dried powder.

As used herein, the term "carrier" refers to a solid material that is utilized in a spray dryable liquid composition, containing liquid and the product to be spray dried, to carry and at least partially support or at least partially encapsulate the product in the spray dried powder resulting from the spray drying operation. Carriers thus may be associated with the product material in spray dried powders, e.g., as a substrate, support, or associative matrix for the product material. Carriers used in spray drying operations may be of widely varying types, and may include, for example, the starch carriers disclosed in the aforementioned U.S. Pat. Nos. 8,939,388, 9,332,776, and 9,551,527. More generally, carriers such as those listed in Table 1 below illustrate specific carrier materials.

TABLE 1

| Spray Drying Carriers |
|---|
| Polysaccharides: |
| starches, modified food starches, native starches, maltodextrins, alginates, pectins, methylcellulose, ethylcellulose, hydrocolloids, inulin, carbohydrates, mono-, di- and tri-saccharides, soluble fibers, polydextrose |
| Proteins: |
| animal proteins, plant proteins, caseinates, gelatins, soy proteins, pea proteins, whey proteins, milk proteins |
| Gums: |
| guar gum, xanthan gum, *acacia* gum (gum arabic), gellan gum, and caragenan |
| Esters: |
| Polysorbates, stearic acid esters, oleic acid esters |
| Lipids and waxes: |
| coconut oil, medium chain triglyceride (MCT) oils, vegetable oils, sunflower oils, palm oils, caruba waxes, bee waxes |

As used herein, the term "carrier-free" in reference to a spray dryable liquid composition means a spray dryable liquid composition that is devoid of a carrier therein, and "carrier-free" in reference to a spray drying process means a spray drying process carried out in the absence of a carrier in the spray drying operation.

In one aspect, the present disclosure relates to a spray drying process for drying a spray dryable liquid composition to a spray dried powder, wherein the spray dryable liquid composition contains no carrier, the process comprising:

providing the spray dryable liquid composition at a solids concentration not exceeding 80% by weight, based on total weight of the spray dryable liquid composition;

atomizing the spray dryable liquid composition to generate an atomized spray of liquid particles of the spray dryable liquid composition into a spray drying chamber;

flowing a stream of drying fluid at temperature not exceeding 100° C. into the spray drying chamber for flow through the spray drying chamber, to contact the spray of liquid particles therein for drying of the liquid particles to form the spray dried powder; and discharging from the spray drying chamber effluent drying fluid and the spray dried powder dried by contact with the drying fluid in the spray drying chamber.

The spray drying processes of the present disclosure may be carried out with carrier-free spray dryable liquid compositions containing any of a variety of product materials, e.g., at least one product material selected from the group consisting of food materials, beverage materials, fragrance materials, pigment materials, flavor materials, pharmaceutical materials, therapeutic materials, medication materials, homeopathic materials, biological materials, probiotic materials, construction materials, formulating materials, and mixtures, blends, composites, and combinations of two or more different materials of the foregoing.

Specific product materials in the spray dryable liquid composition may for example include at least one product material selected from the group consisting of apple juice, tea, coffee, pear juice, amino acids, fruit purées, pectin, beef broths, gelatin, pharmaceutical products, beet juice, grape juice, pineapple juice, betacyclodextran, lime juice, skim milk, carrageenan, liquid egg, sugars, cheese whey, beers, low alcohol beer, vegetable juices, chicken broth, mango juice, whey protein, citrus juice, orange juice, and whole milk.

In specific embodiments, the spray dryable liquid composition may comprise a juice. In other embodiments, the spray dryable liquid composition may comprise an alcoholic spirit, mash mixture, or pot liquor. In still other embodiments, the spray dryable liquid composition may comprise a comestible or beverage or a precursor thereof. In various other embodiments, the spray dryable liquid composition may comprise coffee. In yet other embodiments, the spray dryable liquid composition may comprise tea.

The carrier-free spray dryable liquid compositions in the broad practice of the present disclosure may comprise any additional non-carrier ingredients, in addition to the product material and liquid. Such additional non-carrier ingredients may include adjuvants, excipients, surfactants, anti-agglomerating agents, anti-caking agents, coactive ingredients, wetting agents, dispersants, emulsifiers, stabilizers, antioxidants, preservatives, poor-forming agents, hardeners, and mixtures, blends, composites, and combinations of two or more ingredients of such types.

The spray dried powder that is produced by the spray drying process and apparatus of the present disclosure may be in any suitable morphological and physical forms, including spherical, spheroidal, polygonal, cuboidal, rod, fiber, helical, dendritic, and any other spatial forms, and may be of any suitable particle size distribution appropriate to the spray dried powder.

The process of the present disclosure as broadly specified above involves flowing a stream of drying fluid at temperature not exceeding 100° C. into the spray drying chamber for flow through the spray drying chamber, to contact the spray of liquid particles therein for drying of the liquid particles to form the spray dried powder. It will be appreciated that in specific implementations of such process, the temperature of the drying fluid stream flowed into the spray drying chamber may be widely varied within such maximum temperature constraints. For example, the temperature of the stream of drying fluid flowed into the spray drying chamber may in various embodiments be below at least one of 100° C., 99° C., 98° C., 95° C., 90° C., 85° C., 80° C., 75° C., 70° C., 65° C., 60° C., 55° C., 50° C., 45° C., 40° C., 30° C., 25° C., 22° C., 20° C., 18° C., 16° C., 15° C., 14° C., 13° C., 12° C., 11° C., and 10° C., and such temperature is above freezing point of the liquid in the spray dryable liquid composition.

In various embodiments, the temperature of the stream of drying fluid flowed into the spray drying chamber may be in a range in which the lower end point of the range is any one of 0° C., 1° C., 2° C., 3° C., 4° C., 5° C., 6° C., 7° C., 8° C., 9° C., 10° C., 11° C., 12° C., 13° C., 14° C., 15° C., 16° C., 18° C., 20° C., 22° C., and 25° C., and in which the upper end point of the range is greater than the lower end point of the range, and is any one of 10° C., 11° C., 12° C., 13° C., 14° C., 15° C., 16° C., 18° C., 20° C., 22° C., 25° C., 30° C., 40° C., 45° C., 50° C., 55° C., 60° C., 65° C., 70° C., 75° C., 80° C., 85° C., 90° C., 95° C., 98° C., 99° C., or 100° C. for example, the temperature of the stream of drying fluid flowed into the spray drying chamber may be in a range of 1° C. to 95° C., 5° C. to 90° C., 10° C. to 80° C., or 15° C. to 65° C., in particular applications.

In the process of the present disclosure as variously described herein, the stream of drying fluid flowed into the spray drying chamber may have a relative humidity that is at or below a predetermined level for the specific application. In various embodiments, the stream of drying fluid flowed into the spray drying chamber may have a relative humidity that does not exceed 35%, 30%, 25%, 20%, 15%, 12%, 10%, 8%, 6%, 5%, 4%, 3%, 2.5%, 2%, 1.8%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, 0.05%, 0.02%, or 0.01%.

In various embodiments, the relative humidity of the stream of drying fluid flowed into the spray drying chamber may be in a range in which the lower end point of the range is any one of $10^{-4}$%, $10^{-3}$%, $10^{-2}$%, $10^{-1}$%, 1%, 1.5%, or 2%, and in which the upper end point of the range is greater than the lower end point of the range, and is any one of 35%, 30%, 20%, 15%, 12%, 10%, 8%, 6%, 5%, 4%, 3%, 2.5%, 2%, 1.8%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, 0.05%, 0.02%, 0.01%, or 0.05%. For example, the stream of drying fluid flowed into the spray drying chamber has a relative humidity in a range of $10^{-4}$% to 35%, $10^{-3}$% to 18%, 0.005 to 17%, 0.01% to 15%, 0.01 to 5%, 0.1 to 5%, or 0.001% to 2%.

The drying fluid in the practice of the process of the present disclosure may be of any suitable type, and may for example comprise gas selected from the group consisting of air, oxygen, oxygen-enriched air, nitrogen, helium, noble gases, carbon dioxide, carbon monoxide, and combinations of two or more of the foregoing. For example, the drying fluid may comprise oxygen, oxygen-enriched air, nitrogen, helium, argon, neon, carbon dioxide, carbon monoxide, or other fluid species, including single component fluids, as well as fluid mixtures. The drying fluid may in various applications exist in a gaseous or vapor form, and the fluid should be constituted to provide an appropriate mass transfer driving force for passage of solvent or other desirably volatilizable material from the atomized sprayed droplets to the drying fluid.

The liquid in the spray dryable liquid composition may likewise be of any suitable type and may for example comprise liquid selected from the group consisting of consisting of water, inorganic solvents, organic solvents, and combinations thereof. In various embodiments, organic solvents may be employed, such as for example acetone, chloroform, methanol, methylene chloride, ethanol, dimethyl formamide (DMF), dimethyl sulfoxide (DMS), glycerine, ethyl acetate, n-butyl acetate, and mixtures with water of the one or more of the foregoing. Such organic solvents may for example be used in spray drying of spray dryable compositions including protein-based materials. In specific embodiments, solvent selected from the group consisting of water, alcohols, and water-alcohol solutions may be advantageously employed.

Spray dryable liquid compositions in the practice of the spray drying process variously described herein may have any suitable physicochemical properties appropriate to the spray drying operation involving the particular material being spray dried. By way of example, the spray dryable liquid composition may have a viscosity in a range of from 50 mPa-s to 28,000 mPa-s.

In various embodiments, the spray dryable liquid composition may have a viscosity that is in a range in which a lower limit of the range is any one of 325, 340, 350, 375, 400, 450, 500, 550, 600, 650, 700, 750, 800, 850, 900, 950, and 1000 mPa-s, and in which an upper limit of the range is greater than the lower limit and is any one of 400, 450, 500, 550, 600, 650, 700, 750, 800, 850, 900, 950, 1000, 2000, 3000, 4000, 5000, 6000, 7000, 8000, 9000, 10,000, 11,000, 12,000, 13,000, 14,000, 15,000, 16,000, 17,000, 18,000, 19,000, and 20,000 mPa-s. As a further specific example, the spray dryable liquid composition may have a viscosity in a range of from 50 to 5000 mPa-s. Viscosity values may be determined in specific applications and implementations using any suitable viscosity-determination methods and viscometry equipment, such as viscometers and rheometers of appropriate types.

It will therefore be appreciated that the viscosity of the spray dryable liquid composition in the spray drying processes of the present disclosure may be widely varied, depending on the specific product material, liquid, and spray drying apparatus employed, as well as the solids concentration in the spray dryable liquid composition. Spray dryable liquid compositions of any suitable solids concentration character may be employed. In various embodiments, the spray dryable liquid composition may have a solids concentration in a range of from 45% to 75% by weight, based on total weight of the spray dryable liquid composition. In other embodiments, the spray dryable liquid composition may have a solids concentration in a range of from 50% to 70% by weight, based on total weight of the spray dryable liquid composition.

In order to enhance the spray drying operation involving the carrier-free spray dryable liquid composition, it may be advantageous in various implementations to generate localized turbulence at multiple loci in the spray drying chamber, to achieve highly efficient drying of the spray dryable liquid composition in the spray drying chamber. Such localized turbulence may be generated by injection of secondary drying fluid into the spray drying chamber, e.g., from injection jets positioned at corresponding openings in the wall of the spray drying chamber, and/or interiorly in the spray drying chamber, to provide enhancement of mass transfer and diffusivity in relation to volatilization of liquid from the sprayed atomized droplets of the spray dryable liquid composition.

As another option that may be useful to enhance spray drying operation, the spray drying process in various embodiments as described herein may further comprise applying an electrohydrodynamic charge (typically referred to misnomerically as electrostatic charge, with corresponding spray drying commonly referred to as electrostatic spray drying) to at least one of the spray dryable liquid composition and the atomized spray of liquid particles, for electrohydrodynamic spray drying of the spray dryable liquid composition. Such electrohydrodynamic spraying operation may be carried out at any suitable voltage conditions appropriate to the specific application in which electrohydrodynamic spraying is employed. In various embodiments, the electrohydrodynamic charge may be in a range of from 0.25 to 80 kV although it will be appreciated that higher or lower electrohydrodynamic charge may be imparted to the material to be spray dried in specific applications. In various embodiments, electrohydrodynamic charge imparted to the particles being spray dried may be in a range of from 0.5 to 75 kV, or from 5 to 60 kV, or from 10 to 50 kV, or in other suitable range or other specific value.

In other embodiments of electrohydrodynamic spray drying conducted in accordance with the present disclosure, the feedstock liquid composition may be sprayed through an electrohydrodynamic nozzle operatively coupled with a voltage source arranged to apply a cyclically switched voltage to the nozzle, e.g., between high and low voltages that are within any of the above-discussed, or other, voltage ranges.

Post atomization charging of the spray dryable composition droplets may be carried out with corona discharge-type atomizers which use an external electrode with the nozzle grounded, or, if the conductivity characteristics of the spray dryable composition droplets are favorable, such post atomization charging may be carried out with electron beam irradiation of the atomized droplets.

Thus, electrohydrodynamic charging of the spray dryable liquid composition may be carried out before, during, or after atomization of such composition. Electrohydrodynamic spraying equipment of widely varying types may be utilized in electrohydrodynamic spraying systems and operations in accordance with the present disclosure, e.g., an electrohydrodynamic spraying device positioned to introduce an electrohydrodynamically charged spray of the spray dryable liquid composition into the interior volume of a spray drying vessel for contacting with drying fluid therein.

The spray dryable liquid composition constituting the feedstock to the spray drying system may be the product of an upstream processing operation, in which a feedstock precursor composition may be processed to provide the spray dryable liquid composition of appropriate or otherwise desired character. In various embodiments, the upstream processing operation may concentrate the feedstock precursor composition so that it has a higher concentration of the product material in a liquid than the concentration of the product material in the feedstock precursor composition. For this purpose, any suitable concentration method and apparatus may be employed. Examples of suitable concentration techniques and apparatus that may be employed include forward osmosis, reverse osmosis, frame and plate heat exchangers, evaporators, spinning cones, osmosis evaporation, chromatography, filtration, nanofiltration, distillation, crystallization, vacuum separation, absorption, and adsorption, as well as suitable combinations of two or more of the foregoing.

Correspondingly, the spray dried powder produced by the carrier-free spray drying process of the present disclosure may be further treated by a downstream treatment process of suitable type, e.g., for further drying, development of performance characteristics (such as flavor, taste, or aroma characteristics in the case of flavor spray dried powders, for example), mixing with other powder ingredients to form end-product powder mixtures, granulation, micronizing, or other sizing or morphological processing, lyophilization, dispersion, blending, irradiation, and/or a wide variety of other downstream processing operations to produce an intermediate or end-use product for an intended application or field of use.

The effluent drying fluid that is discharged from the spray drying chamber in the carrier-free spray drying process of the present disclosure may correspondingly be further treated or processed. In various embodiments, the effluent drying fluid discharged from the spray drying chamber is treated to remove solids therefrom to produce solids-depleted drying fluid, and the solids-depleted drying fluid is recycled as drying fluid in the stream of drying fluid flowed into the spray drying chamber. The effluent drying fluid may additionally or alternatively be treated or processed in the spray drying system to render it of appropriate character for other uses outside the spray drying system and operation, or for effluent discharge to the ambient environment of the spray drying system or to the atmosphere.

In various embodiments, the effluent drying fluid discharged from the spray drying chamber is treated to remove solids therefrom in a cyclone separator or other solids-fluid separator followed by flow of the effluent drying fluid through a bag filter or other filter assembly or filter medium to produce the solids-depleted drying fluid of desired character for recycle and/or ultimate discharge.

When recycled to the spray drying chamber for flow therethrough, the solids-depleted drying fluid may be treated to adjust the characteristics thereof, e.g., temperature and/or relative humidity characteristics.

The spray dried powder produced by the carrier-free spray drying process may be dried to any suitable powder characteristics. For example, in various embodiments, the spray drying process may be conducted in the spray drying system to produce spray dried powder discharged from the spray drying chamber in which the amount of liquid in the spray dried powder discharged from the spray drying chamber is below at least one of 10, 9, 8, 7, 6, 5, 4, 3, 2, 1, 0.5 and 0.1 wt. % liquid, based on total weight of the spray dried powder. In various embodiments, the spray drying process may be carried out and the spray drying system may be operated, to produce spray dried powder discharged from the spray drying chamber having liquid content in a predetermined range, e.g., in a range of 5-8 wt. %, 2-3 wt. %, 4-6 wt. %, 5-10 wt. %, based on total weight of the spray dried powder, or liquid content in some other range or subject to some other predetermined maximum liquid content value. The spray dried powder produced in the practice of the present disclosure is of markedly superior character, as regards its powder characteristics and performance characteristics, which in specific instances may include characteristics such as flavor, taste, aroma, solubility, agglomeration resistance, stability, oxidation resistance, degradation resistance, integrity of active product ingredient(s), processability, etc.

In the broad practice of the present disclosure, the apparatus that is utilized to atomize the spray dryable liquid composition to generate an atomized spray of liquid particles of the spray dryable liquid composition into a spray drying chamber may be of any suitable type, and may for example comprise a rotary atomizer, centrifugal atomizer, nebulizer, ultrasonic disperser, nozzle, or a combination of two or more of the foregoing. The liquid composition may be introduced into the interior volume of the spray drying vessel in a liquid film or ligament form that is broken up to form droplets. A wide variety of equipment and techniques is able to be utilized to form the spray of liquid composition in the form of droplets or finely divided liquid particles. Typically, droplet size and distribution may be fairly constant for a given spray drying technique, and in various embodiments may be in a range of 10-300 μm, or other suitable range.

In another aspect, the disclosure relates to a spray drying system constructed and arranged to carry out the carrier-free spray drying process variously described hereinabove.

The spray drying system is shown in an illustrative implementation in FIG. 1 hereof.

As shown, the spray drying system 500 includes a feedstock precursor composition source 502, from which which a feedstock precursor composition is flowed in feed line 504 to a feedstock composition processing unit 506, in which the precursor composition is processed to yield the spray dryable liquid composition. Such upstream processing unit may be of any suitable type as previously discussed herein, and may for example comprise a concentration unit in which the product material to be spray dried is concentrated from a feedstock precursor composition concentration to a higher product material concentration in the spray dryable liquid composition discharged from the unit in line 508.

From the feedstock composition processing unit 506, the carrier-free spray dryable liquid composition is flowed in liquid composition feed line 508 by pump 510 to feedstock feed line 512, from which it flows into the spray dryer inlet 516 of the spray dryer vessel 518, and thereupon is atomized by the atomizer 514 to generate an atomized spray 520 of the spray dryable liquid composition. Concurrently, conditioned drying fluid described more fully hereinafter is flowed in conditioned drying fluid feed line 570 to the inlet 516 of the spray dryer vessel 518, so that the introduced conditioned drying fluid flows through the interior volume 522 of the spray dryer vessel 518, for contact with the atomized spray of carrier-free spray dryable liquid composition.

The conditioned drying fluid, or any portion thereof, may be flowed through the atomizer 514, in a so-called two-fluid atomization, or the conditioned drying fluid may be flowed into the interior volume 522 of the spray drying vessel 518 as a separate stream, in relation to the introduction of the carrier-free spray dryable liquid composition and its passage through the atomizer 514.

The atomizer 514 may be of any suitable type, and may for example include any of rotary atomizers, centrifugal atomizers, jet nozzle atomizers, nebulizers, ultrasonic atomizers, etc., and combinations of two or more of the foregoing. The atomizer may be electrohydrodynamic to carry out electrohydrodynamic spray drying of the concentrated feedstock composition, or the atomizer may be non-electrohydrodynamic in character.

Regardless of the specific atomizer type and mode of atomization employed, the atomized spray 520 of concentrated feedstock composition is introduced to the interior volume 522 of the spray drying vessel 518, and the atomized droplets of the carrier-free spray dryable liquid composition are contacted with the conditioned drying fluid during their passage through the interior volume to the spray dryer outlet 524, to dry the atomized droplets and produce the spray dried dry powder product.

The spray drying vessel 518 may optionally be provided with auxiliary drying fluid peripheral feed lines 526, in which the arrowheads of the respective schematic feed lines 526 designate injector jets arranged to introduce auxiliary drying fluid into the interior volume 522 of the spray drying vessel 518. The feed lines 526 and injector jets thereof thus may pass through corresponding wall openings in the spray drying vessel 518 so that the injector jets are internally arrayed, or the injector jets may be arranged so that they communicate with wall openings in the spray drying vessel, injecting auxiliary drying fluid therethrough into the interior volume 522. The auxiliary drying fluid may be introduced into the interior volume of the spray drying vessel at sufficient pressure and flow rate to generate localized turbulence 530 at or near the point of introduction into the interior volume of the spray drying vessel.

The auxiliary drying fluid peripheral feed lines 526 are illustrated as being coupled with an auxiliary drying fluid manifold 528 through which the auxiliary drying fluid is flowed to the respective feed lines 526. The auxiliary drying fluid may be introduced into the interior volume of the spray drying vessel in a continuous manner, or in an intermittent manner. The auxiliary drying fluid may be introduced in bursts, e.g., in a time-sequenced manner, and the injector jets may be programmably arranged under the monitoring and control of a central processor unit such as the CPU 590 illustrated in FIG. 1.

Such localized induction of turbulence is highly effective in enhancing the diffusivity and mass transfer of liquid from the atomized droplets of concentrated feedstock composition to the drying fluid present in the spray drying vessel.

The spray drying vessel 518, as a further enhancement of the drying of the atomized droplets of concentrated feedstock composition in the interior volume of the vessel, may be equipped with an auxiliary drying fluid central feed line 532 as shown. The auxiliary drying fluid central feed line 532 is provided with a series of longitudinally spaced-apart auxiliary drying fluid central feed line injector jets 534, in which auxiliary drying fluid may be injected under sufficient pressure and flow rate conditions to generate auxiliary drying fluid injected turbulence regions 536.

As discussed above with respect to the auxiliary drying fluid introduced into the interior volume of the spray drying vessel through the feed lines 526 and associated injector jets, the auxiliary drying fluid may be introduced into the interior volume of the spray drying vessel in a continuous manner, or in an intermittent manner from the injector jets 534, to provide auxiliary drying fluid injected turbulence regions 536 at a central portion of the interior volume 522 in the spray drying vessel. As discussed in connection with the peripheral feed lines and associated injector jets, the auxiliary drying fluid may be introduced through the central feed line injector jets 534 in bursts, e.g., in a time-sequenced manner, and the injector jets may be programmably arranged under the monitoring and control of a central processor unit such as the CPU 590 illustrated in FIG. 1.

A combination of peripheral jets and central jets such as shown in FIG. 1 may be used to provide localized turbulence in the central region as well as the outer wall region of the interior volume in the spray dryer vessel, and effects a remarkably efficient spray drying process, in which anomalous flow behavior, such as dead zones or stagnant regions in the interior volume, is minimized. A highly favorable hydrodynamic mass transfer environment is correspondingly provided, and the spray dryer vessel as a result of such localized turbulence generation capability can be substantially reduced in size and associated footprint, thereby enabling smaller pumps, compressors, blowers and other associated ancillary equipment to be employed, with consequent enhancement of the capital equipment and operating cost characteristics of the concentration and spray drying system.

The spray dried powder and effluent drying gas that are produced by the contacting of the atomized droplets of concentrated feedstock composition with drying fluid in the interior volume of the spray dryer vessel, are discharged from the spray dryer vessel in spray dryer outlet 524 and flow in spray dryer effluent line 538 to cyclone 540. In lieu of cyclone equipment, any other suitable solids/gas separation unit of appropriate character may be employed. The cyclone 540 separates dried solids from the drying fluid, with the dried solids flowing in dried solids discharge line 542 to a dried solids collection vessel 544. The drying fluid depleted in solids content flows from the cyclone in drying fluid discharge line 546, flowing through fines filter 548 to condenser 550. In the condenser 550, the drying fluid is cooled, resulting in condensation of condensable gas therein, with condensate being discharged from the condenser in condensate discharge line 552.

The resulting condensate-depleted drying fluid then flows in drying fluid recycle line 554 containing pump 556 therein to the drying fluid conditioning assembly 568, together with any needed make-up drying fluid introduced in drying fluid make-up feed line 610. The drying fluid conditioning assembly conditions the recycle drying fluid and any added make-up drying fluid for flow to the spray dryer vessel 518 in conditioned drying fluid feed line 570. The drying fluid conditioning assembly may comprise a dehumidifier and/or heat exchange (heater/cooler) equipment to provide drying fluid for recycle at appropriate desired conditions of temperature and relative humidity.

Thus, drying fluid, including any necessary make-up drying fluid, may be provided to the drying fluid conditioning assembly 568, or otherwise provided to the spray drying system at other appropriate location(s) in the system, from an appropriate source, and with any appropriate preconditioning operations being carried out by associated equipment or devices, as needed to conduct the spray drying operation at the desired temperature, pressure, flow rate, composition, and relative humidity. Thus, for example, make-up drying fluid may be provided to the conditioning assembly 568 from a tank, storage vessel, or other source (e.g., the ambient atmosphere, in the case of air as such drying fluid).

As a source of auxiliary drying fluid in the system, a portion of the recycled drying fluid from drying fluid recycle line 554 may be diverted in auxiliary drying fluid feed line 572 containing flow control valve 574, to the auxiliary drying fluid conditioning assembly 576. The auxiliary drying fluid conditioning assembly 576 may be constructed and arranged in any suitable manner, and may be of a same or similar character to the construction and arrangement of the drying fluid conditioning assembly 568. The auxiliary drying fluid conditioning assembly 576 thus conditions the auxiliary drying fluid so that it is at appropriate condition for the use of the auxiliary drying fluid in the system.

The conditioned auxiliary drying fluid flows from auxiliary drying fluid conditioning assembly 576 through auxiliary drying fluid feed line 578, from which it flows in auxiliary drying fluid feed line 580 containing pump 582 to the manifold 528, while the remainder of the conditioned auxiliary drying fluid flows in auxiliary drying fluid feed line 578 to pump 584, from which it is flowed in auxiliary drying fluid feed line 586 to the auxiliary drying fluid central feed line 532, for introduction in the central region of the interior volume of the spray dryer vessel, as previously described.

It will be recognized that the system shown in FIG. 1 could be alternatively constructed and arranged with the drying fluid conditioning assembly 568 processing both the main flow of drying fluid and the auxiliary drying fluid, without the provision of a separate auxiliary drying fluid conditioning assembly 576, e.g., when the main drying fluid and auxiliary drying fluid are of a substantially same character with respect to their relevant fluid characteristics. It will also be recognized that separate flow circulation loops for each of the main drying fluid and auxiliary drying fluid may be provided, when the main drying fluid and auxiliary drying fluid are or comprise different gases, or are otherwise different in their relevant fluid characteristics.

The FIG. 1 system is shown as including a central processor unit (CPU) 590 arranged to conduct monitoring and/or control operations in the system, and when employed in a controlling aspect, may be employed to generate control signals for modulation of equipment and/or fluids conditions, to maintain operation at set point or otherwise desired operational conditions. As mentioned, the CPU could be operationally connected to the conditioning assemblies 568 and 576, to control components thereof such as dehumidifiers, thermal controllers, heat exchange equipment, etc.

The CPU 590 is illustratively shown in FIG. 1 as being operatively coupled by monitoring and/or control signal transmission lines 592, 594, 596, 598, 600, 602, and 604 with pump 510, drying fluid conditioning assembly 568, auxiliary drying fluid conditioning assembly 576, flow control valve 574, pump 582, pump 556, and pump 584, respectively.

It will be recognized that the specific arrangement of the CPU shown in FIG. 1 is of an illustrative character, and that the CPU may be otherwise arranged with respect to any components, elements, features, and units of the overall system, including the concentration unit 506, to monitor any suitable operational components, elements, features, units, conditions, and parameters, and/or to control any suitable operational components, elements, features, units, conditions, parameters, and variables. For such purpose, as regards monitoring capability, the system may comprise appropriate sensors, detectors, components, elements, features, and units. The signal transmission lines may be bidirectional signal transmission lines, or may constitute cabling including monitoring signal transmission lines and separate control signal transmission lines.

It will be appreciated that the spray drying system of the present disclosure affords arrangements in which the contacting gas, auxiliary contacting gas, drying fluid, and auxiliary drying fluid, or any two or more thereof, may have a substantially same composition, temperature, and/or relative humidity, thereby achieving capital equipment and operating cost efficiencies with corresponding simplification of the system requirements. Thus, for example, all of the contacting gas, auxiliary contacting gas, drying fluid, and auxiliary drying fluid may be air, nitrogen, argon, or other gas from a common gas source, and such common gas may be provided at a substantially same temperature and relative humidity, so that common thermal conditioning and dehumidification equipment can be employed.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A spray drying process for drying a spray dryable liquid composition to a spray dried powder, wherein the spray dryable liquid composition contains no carrier, the process comprising:
   providing the spray dryable liquid composition at a solids concentration of at least 45% by weight but not exceeding 80% by weight, based on total weight of the spray dryable liquid composition;

atomizing the spray dryable liquid composition to generate an atomized spray of liquid particles of the spray dryable liquid composition into a spray drying chamber;

flowing a stream of drying fluid at a temperature not exceeding 100° C. into the spray drying chamber for flow through the spray drying chamber, to contact the spray of liquid particles therein for drying of the liquid particles to form the spray dried powder; and discharging from the spray drying chamber effluent drying fluid and the spray dried powder dried by contact with the drying fluid in the spray drying chamber, wherein said atomizing is carried out so that the atomized spray of liquid particles of the spray dryable liquid composition comprise droplets of the spray dryable liquid composition having a droplet size in a range of from 10 to 300 μm.

2. The process of claim 1, wherein the spray dryable liquid composition comprises at least one product material selected from the group consisting of food materials, beverage materials, fragrance materials, pigment materials, flavor materials, pharmaceutical materials, therapeutic materials, medication materials, homeopathic materials, biological materials, probiotic materials, construction materials, formulating materials, and mixtures, blends, composites, and combinations of two or more different materials of the foregoing.

3. The process of claim 1, wherein the spray dryable liquid composition comprises at least one product material selected from the group consisting of apple juice, tea, coffee, pear juice, amino acids, fruit purees, pectin, beef broths, gelatin, pharmaceutical products, beet juice, grape juice, pineapple juice, betacyclodextran, lime juice, skim milk, carrageenan, liquid egg, sugars, cheese whey, beers, low alcohol beer, vegetable juices, chicken broth, mango juice, whey protein, citrus juice, orange juice, and whole milk.

4. The process of claim 1, wherein the spray dryable liquid composition comprises a juice.

5. The process of claim 1, wherein the spray dryable liquid composition comprises an alcoholic spirit, mash mixture, or pot liquor.

6. The process of claim 1, wherein the spray dryable liquid composition comprises a comestible or beverage or a precursor thereof.

7. The process of claim 1, wherein the spray dryable liquid composition comprises coffee.

8. The process of claim 1, wherein the spray dryable liquid composition comprises tea.

9. The process of claim 1, wherein the temperature of the stream of drying fluid flowed into the spray drying chamber is below at least one of 100° C., 99° C., 98° C., 95° C., 90° C., 85° C., 80° C., 75° C., 70° C., 65° C., 60° C., 55° C., 50° C., 45° C., 40° C., 30° C., 25° C., 22° C., 20° C., 18° C., 16° C., 15° C., 14° C., 13° C., 12° C., 11° C., and 10° C., and said temperature is above freezing point of the liquid in the spray dryable liquid composition.

10. The process of claim 1, wherein the temperature of the stream of drying fluid flowed into the spray drying chamber is in a range in which the lower end point of the range is any one of 0° C., 1° C., 2° C., 3° C., 4° C., 5° C., 6° C., 7° C., 8° C., 9° C., 10° C., 11° C., 12° C., 13° C., 14° C., 15° C., 16° C., 18° C., 20° C., 22° C., and 25° C., and in which the upper end point of the range is greater than the lower end point of the range, and is any one of 10° C., 11° C., 12° C., 13° C., 14° C., 15° C., 16° C., 18° C., 20° C., 22° C., 25° C., 30° C., 40° C., 45° C., 50° C. 55° C., 60° C., 65° C., 70° C., 75° C., 80° C., 85° C., 90° C., 95° C., 98° C., 99° C., or 100° C.

11. The process of claim 1, wherein the spray dryable liquid composition has a viscosity in a range of from 50 to 5000 mPa-s, and a solids concentration in a range of from 45% to 75% by weight, based on total weight of the spray dryable liquid composition.

12. The process of claim 1, wherein amount of liquid in the spray dried powder discharged from the spray drying chamber is below at least one of 10, 9, 8, 7, 6, 5, 4, 3, 2, 1, 0.5 and 0.1 wt. % liquid, based on total weight of the spray dried powder.

13. The process of claim 1, the spray dryable liquid composition comprises at least one food, beverage, or flavor product material.

14. The process of claim 1, further comprising generating localized turbulence at multiple loci in the spray drying chamber, to enhance drying of the spray dryable liquid composition in the spray drying chamber.

15. The process of claim 14, wherein said spray drying chamber comprises an outer wall enclosing an interior volume of the spray drying chamber, and said multiple loci comprise an outer wall region of the interior volume of the spray drying chamber.

16. The process of claim 14, wherein said spray drying chamber comprises an interior volume, and said multiple loci comprise a central region of the interior volume of the spray drying chamber.

17. The process of claim 14, wherein said spray drying chamber comprises an outer wall enclosing an interior volume of the spray drying chamber, and said multiple loci comprise (i) an outer wall region of the interior volume of the spray drying chamber and (ii) a central region of the interior volume of the spray drying chamber.

18. The process of claim 14, wherein said generating localized turbulence at multiple loci in the spray drying chamber comprises injecting auxiliary drying fluid at said multiple loci to generate said localized turbulence.

19. The process of claim 18, wherein each of said drying fluid and said auxiliary drying fluid comprises air, oxygen, oxygen-enriched air, or nitrogen.

20. The process of claim 18, wherein each of (i) the stream of drying fluid flowed into the spray drying chamber and (ii) the auxiliary drying fluid injected at said multiple loci has a relative humidity in a range in which the lower end point of the range is any one of $10^{-4}$%, $10^{-3}$%, $10^{-2}$%, $10^{-1}$%, 1%, 1.5%, or 2%, and in which the upper end point of the range is greater than the lower end point of the range, and is any one of 35%, 30%, 20%, 15%, 12%, 10%, 8%, 6%, 5%, 4%, 3%, 2.5%, 2%, 1.8%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, 0.05%, 0.02%, 0.01%, or 0.05%.

* * * * *